United States Patent [19]

Muroi et al.

[11]  4,368,105
[45]  Jan. 11, 1983

[54] ELECTROLYTIC SOLUTION FOR KARL FISCHER COULOMETRIC TITRATION

[75] Inventors: Kaname Muroi, Machida; Hiroko Fujino, Yamato, both of Japan

[73] Assignee: Mitsubishi Chemical Industries Limited, Japan

[21] Appl. No.: 226,732

[22] Filed: Jan. 21, 1981

[30] Foreign Application Priority Data

Feb. 12, 1980 [JP] Japan .................................. 55-15735

[51] Int. Cl.$^3$ ............................................ G01N 27/44
[52] U.S. Cl. ................................. 204/1 T; 204/195 T
[58] Field of Search .................. 204/1 T, 1 M, 195 T; 23/230 R, 232 E

[56] References Cited

U.S. PATENT DOCUMENTS 3,749,659  7/1973  Dahms ............................ 204/195 T
4,049,503  9/1977  Becker et al. ................... 204/195 S

FOREIGN PATENT DOCUMENTS 55-98350  7/1980  Japan.

OTHER PUBLICATIONS

Pre-print of Japan Analytical Chemical Soc. 28th Symposium.
Pre-print of Japan Chemical Society 31st Autumal Symposium.

Primary Examiner—T. Tung
Attorney, Agent, or Firm—Jordan B. Bierman; Linda Bierman

[57]  ABSTRACT

There is disclosed an electrolytic solution for Karl Fischer method comprising chloroform and an alkylene carbonate as solvent and iodine or an iodide, sulfur dioxide, pyridine and a small amount of an alcohol. The solution is suitable for use in determination of water by Karl Fischer titration method as a generating medium.

9 Claims, No Drawings

ELECTROLYTIC SOLUTION FOR KARL FISCHER COULOMETRIC TITRATION

FIELD OF THE INVENTION

This invention relates to an electrolytic solution for Karl Fischer coulometric titration, in particular to an electrolytic solution for use in determination of a very small amount of water in a ketone. In this specification and claims, "electrolytic solution" means a generating medium used in a generator solution cell.

DESCRIPTION OF PRIOR ART

Karl Fischer method is determination of a water content of various materials with a Karl Fischer reagent which comprises iodine, sulfur dioxide, pyridine and methanol and which selectively and quantitatively reacts with water according to the following equations:

$$SO_2 + I_2 + H_2O + 3C_5H_5N \rightarrow 2C_5H_5N \cdot HI + C_5H_5N \cdot SO_3 \qquad \text{I}$$

$$C_5H_5N \cdot SO_3 + CH_3OH \rightarrow C_5H_5N \cdot HSO_4CH_3 \qquad \text{II}$$

The Karl Fischer method is one of the most reliable procedures for determination of water content and is applicable to a wide variety fo materials. This method is used by volumetric titration and coulometric titration.

The volumetric titration is carried out by titrating a sample with a Karl Fischer reagent the strength of which has been standardized and the water content is calculated on the basis of the amount of the reagent consumed. In the coulometric titration, iodine which is essential for reaction with water is formed from an iodide according to the following equation whereby the Karl Fishcer reagent is produced by electrolysis in situ:

$$2I^- - 2e \rightarrow I_2 \qquad \text{III}$$

The amount of iodine produced is accurately proportional to the quantity of electricity required for electrolysis. This makes it possible to determine the amount of water by virtue of the quantity of electricity consumed until the equivalence is reached (the end point). Such coulometric titration method requires an electrolytic solution present in the generator solution cell and a cathode solution, the former being a solution containing an iodide which generates iodine by electrolytic oxidation to obtain a Karl Fischer reagent in situ and the later performing the corresponding reduction.

The titration cell assembly used for coulometric titration comprises a generator solution cell, a cathode solution cell and a membrane separating the cells made of material such as ceramic or ion exchange resin. The membrane must prevent mixing of the two solutions and must have low resistance. The generator solution cell has an electrode for electrolysis and an indicator assembly for detecting the end point of titration and the cathode solution cell has an electrode for electrolysis. The coulometric titration is carried out by charging the electrolytic solution in the generator solution cell and the cathode solution in the cathode solution cell, and the assembly is sealed air tightly. Then, the electrolytic solution is subjected to electrolysis with agitation to change the solution to anhydride state and a sample the water content of which is to be determined is added to the electrolytic solution which is subjected to electrolysis with agitation. The water content is calculated based on the quantity of electricity consumed until the end point.

The determination of the end point of the coulometric titration according to this invention is carried out in two ways of amperometric titration at constant voltage and potentiometric titration at constant current. In the former case, a constant voltage is applied to two platinum electrodes of the indicator assembly and the polarization potential is measured. When water is present in the electrolytic solution, iodine generated by electrolytic oxidation reacts immediately with water to convert into hydrogen iodide. Therefore, if only iodide is present in the solution the indicator electrode is polarized and thus no current is passed through between the platinum electrodes, on the other hand, when titration reaches beyond the equivalence the electrode is depolarized due to the presence of free iodine thereby passing through the current. Therefore, a constant voltage for example 10 to 100 mV is continuously applied to the indicator electrode and at the time when a constant current for example 10 to 20 μA is first detected is the end point. Potentiometric titration at constant current is based on the same theory. A constant current is passed through between two platinum electrodes and when the voltage is suddenly changed, for example, from 300-500 mV to 10-50 mV is the end point.

This method has advantages over the volumetric titration in that, for example, no previous standardization of the reagent is required, a trace amount of water can readily and accurately be determined through feasible and simple procedures and the electrolytic solution can be used repeatedly.

Electrolytic solutions for use in the generator solution cell in coulometric titration are commercially available. For example, Mitsubishi Chemical Industries Limited, Tokyo, Japan produces Aquamicron ® A "MITSUBISHI" (trade name) which contains methanol as solvent. However, such solution is not suitable for determination of water content of a ketone because methanol reacts with ketone to form water involving a ketal reaction as follows:

$$2CH_3OH + R_2CO \rightarrow R_2C(OCH_3) + H_2O \qquad \text{IV}$$

In view of the above, for determination of water in a ketone, it is imperative to use a methanol-free electrolytic solution, for example, Aquamicron ® AK "MITSUBISHI" (trade name) for solvent of which is ethylene glycol and to carry out the operation at a temperature below 15° C.

The inventors have conducted investigation for finding out an electrolytic solution which can be applied to determination of water content in a ketone at room temperature and we have devised this invention.

SUMMARY OF THE INVENTION

One object of this invention is to provide an electrolytic solution for Karl Fischer coulometric titration suitable for use in determination of water content of a ketone at room temperature.

Another object of this invention is to provide an electrolytic solution for Karl Fischer coulometric titration which can be applied to determination of water content of various materials other than a ketone.

A further object is to provide an electrolytic solution having high conductivity for Karl Fischer coulometric titration.

According to this invention there is provided an electrolytic solution for Karl Fischer coulometric titration which solution comprises chloroform and an alkylene carbonate, as major proportion, as well as iodine or an iodide, sulfur dioxide, pyridine and a small amount of an alcohol.

DETAILED DESCRIPTION OF THE INVENTION

As mentioned above, the major proportion (about 80% by weight) of the electrolytic solution according to this invention is comprised of chloroform and an alkylene carbonate as a mixed solvent, the remainder being iodine or an iodide, sulfur dioxide, pyridine and a small amount of an alcohol, as active ingredients. Various materials dissolve in chloroform and chloroform can promote the reactions involved in the Karl Fischer titration. The alkylene carbonate gives conductivity to the electrolytic solution and, in the presence of a small amount of an alcohol, enables the reactions of the Karl Fischer method to proceed to completion. The proportion by weight of alkylene carbonate to chloroform is usually 1:20 to 1:2. Examples of the alkylene carbonate include ethylene carbonate, 1,2-propylene carbonate and 1,2-butylene carbonate. Propylene carbonate is preferred. In general, if the proportion of the alkylene carbonate is low, the water content value which has been detected will be somewhat lower than the true value. On the other hand, where a solution having a high proportion of alkylene carbonate is repeatedly used, it becomes difficult to determine the end point of the reaction accurately. Therefore, where propylene carbonate is employed, the preferred proportion of the carbonate to chloroform is from 1:12 to 1:5.

The preferred iodide is potassium iodide and sodium iodide. The concentration of ingredients in the solution is 0.9 to 1.4% preferably 1.0 to 1.2% by weight, in terms of $I_2$, of iodine or an iodide, 2.5 to 7.5%, preferably 3 to 6.5% by weight of sulfur dioxide and 10 to 15%, preferably 11 to 14% by weight of pyridine. At concentrations of pyridine and sulfur dioxide outside the above ranges, the measured value of water content is liable to be lower than the true value. With an electrolytic solution which does not contain an alcohol, the reaction proceeds to about 90% or more but it does not complete. The presence of a small amount of an alcohol makes it possible for the reaction to proceed to completion and to indicate clearly the end point of the reaction. Examples of alcohol which can be employed in this invention are conveniently an aliphatic alcohol, such as methanol, ethanol, isopropanol, n-, iso- and tert-butanol as well as ethylene glycol, propylene glycol, ethylene glycol monomethyl ether and ethylene glycol monoethyl ether. The amount of the alcohol in the electrolytic solution is usually up to 0.7% by weight and preferably from 0.2 to 0.4% by weight of ethanol. Too low an alcohol content results in a measurement of water content lower than the actual value and vice versa.

Determination of water content using the electrolytic solution according to this invention can be carried out in conventional way. A generator solution cell of a Karl Fischer coulometric titration apparatus is charged with the electrolytic solution of this invention and a cathode solution cell is charged with an appropriate cathode solution comprising the solvent, sulfur dioxide and pyridine. Then, electric current (generating current) is applied to the electrodes to effect electrolytic oxidation thereby removing water present in the electrolytic solution. Then, a sample the water content of which is to be determined is added to the electrolytic solution and electric current is applied again.

Where the electrolytic solution is prepared from iodine, it is essential that water be added to the solution until any red brown originating from iodine disappears thereby forming iodide (presumably hydrogen iodide) before use. The cathode solution may be a commercial product, for example, Aquamicron ® CK "MITSUBISHI." Where a ketone is subjected to a Karl Fischer coulometric titration, since the cathode solution diffuses into the electrolytic solution it is preferred that the cathode solution does not contain any material which is reactive with a ketone, such as methanol.

The electrolytic solution according to this invention can be used for determination of water content of various materials, such as hydrocarbons and silicone oils. It is especially useful at room temperature in the determination of a very small amount of water in acetone in which a ketal reaction is liable to occur. Further, the electrolytic solution has high conductivity to allow passage of a large electrolytic current and, therefore, titration can be carried out with high efficiency.

This invention will be further illustrated in detail by means of the following examples. However, it should be understood that this invention is in no way limited to these examples.

EXAMPLE 1

Electrolytic solutions were prepared by adding to a mixed solvent of 101.6 g of chloroform and 12.1 g of 1,2-propylene carbonate, 17.6 g of pyridine, 5.7 g of sulfur dioxide, 1.6 g of iodine and various alcohols in an amount given in Table 1.

The electrolytic solution was charged in the generator solution cell of a commercial Karl Fischer coulometric titration apparatus, MITSUBISHI Moisture Meter Mode CA-02 available from Mitsubishi Chemical Industries Limited, Tokyo, Japan and a commercial cathode solution, Aquamicron ® CK "MITSUBISHI" was charged in the cathode solution cell. To the electrolytic solution, water was added until the red brown of free-iodine disappeared, and 0.5 ml of acetone to be tested was added. Then, electric current was applied at room temperature to determine the water content. Then, 0.5 ml of acetone was added to the used electrolytic solution to repeat further determination 10 times. The results are given in Table 1.

For comparison, 5 ml of the acetone was added to 30 ml of a mixed solvent of propylene glycol and pyridine (50/50 v/v), and the resulting solution was volumetrically titrated with a commercial Karl Fischer reagent, Karl Fischer reagent SS "MITSUBISHI" at a temperature of 10° to 15° C., the water content of acetone was found to be 0.22% by weight.

TABLE 1

| Sample | Amount (ml) | Water Content (%) |
|---|---|---|
| Methanol | 0.5 | 0.218–0.220 |
| Ethanol | 0.5 | 0.218–0.221 |
| Isopropanol | 1.0 | 0.216–0.220 |
| n-Butanol | 1.0 | 0.217–0.221 |
| Ethylene glycol | 0.7 | 0.217–0.221 |
| Propylene glycol | 0.5 | 0.217–0.219 |
| Ethylene glycol monomethyl ether | 0.7 | 0.215–0.220 |
| Ethylene glycol monoethyl ether | 1.0 | 0.215–0.220 |

Data of Table 1 show that the electrolytic solution for coulometric titration of this invention gives substantially the same results at room temperature irrespective of the type of alcohol added.

EXAMPLE 2

As in Example 1, an electrolytic solution was prepared using ethanol and the water content of methanol, benzene, toluene and formamide was determined. The results are given in Table 2 in which results obtained by using a commercial electrolytic solution, Aquamicron® A "MITSUBISHI", are also given.

TABLE 2

| Sample | Water Content (%) | |
| --- | --- | --- |
|  | This Invention | Aquamicron A |
| Methanol | 0.0203 | 0.0208 |
| Benzene | 0.0219 | 0.0223 |
| Toluene | 0.0142 | 0.0146 |
| Formamide | 0.0487 | 0.0498 |

Data of Table 2 show that the electrolytic solution of this invention can also be applied to various materials and its performance is comparable with the commercial product.

EXAMPLE 3

An electrolytic solution was prepared by adding 17.6 g of pyridine, 5.7 g of surfur dioxide and 1.6 g of iodine to a mixed solvent of 110 g of chloroform and 6 g of ethylene carbonate and adding 0.5 g of ethanol to the resulting mixture.

With the procedures and the acetone used in Example 1, the water content of the acetone was determined at room temperature. The test was repeated 10 times with the same electrolytic solution. The water contents obtained were within a range of from 0.217 to 0.221%.

What is claimed is:

1. An electrolytic solution for Karl Fischer coulometric titration the major proportion being comprised of chloroform and an alkylene carbonate, as solvent, and the remainder being iodine or an iodide, sulfur dioxide, pyridine and a small amount of an alcohol.

2. An electrolytic solution in accordance with claim 1, wherein the proportion by weight of said alkylene carbonate to said chloroform is within a range of from 1:20 to 1:2.

3. An electrolytic solution in accordance with claims 1 or 2, wherein the content of said pyridine is 10 to 15% by weight.

4. An electrolytic solution in accordance with claims 1 or 2, wherein the content of said sulfur dioxide is 2.5 to 7.5% by weight.

5. An electrolytic solution in accordance with claims 1, or 2, wherein the content of said iodine or iodide is 0.9 to 1.4% by weight, in terms of $I_2$.

6. An electrolytic solution in accordance with claims 1, 2, wherein the content of said alcohol is up to 0.7% by weight.

7. An electrolytic solution in accordance with claims 1, wherein said alkylene carbonate is propylene carbonate.

8. An electrolytic solution in accordance with claim 7 wherein the proportion by weight of said propylene carbonate to said chloroform is 1:12 to 1:5.

9. An electrolytic solution in accordance with claim 2 wherein said alkylene carbonate is propylene carbonate.

* * * * *

UNITED STATES PATENT OFFICE
CERTIFICATE OF CORRECTION

PATENT NO. : 4,368,105
DATED : January 11, 1983
INVENTOR(S) : Muroi, et al

It is certified that error appears in the above-identified patent and that said Letters Patent are hereby corrected as shown below:

Column 6, Claims 3 and 4, change "1 or 2" to --1, 2, 7 or 9--

Claim 5, change "1, or 2" to --1, 2, 7 or 9--

Claim 6, after "1, 2," insert --7 or 9,--

Claim 7, change "Claims" to --Claim--

Claim 8, change "Claim 7" to --Claims 7 or 9--

Signed and Sealed this

Thirteenth Day of September 1983

[SEAL]

Attest:

Attesting Officer

GERALD J. MOSSINGHOFF
Commissioner of Patents and Trademarks